United States Patent [19]

Ford, Jr. et al.

[11] 4,350,163
[45] Sep. 21, 1982

[54] METHOD AND APPARATUS FOR ANALYZING CONTAMINANTS IN AQUEOUS HUMOR

[76] Inventors: Norman C. Ford, Jr., 85 N. Whitney St., Amherst, Mass. 01002; David K. Dueker, 11 Rangeley Ridge, Winchester, Mass. 01890

[21] Appl. No.: 154,432

[22] Filed: May 29, 1980

[51] Int. Cl.³ .................... A61B 3/00; A61B 5/00
[52] U.S. Cl. .................... 128/633; 128/745; 351/1; 351/39
[58] Field of Search .................... 128/633, 737, 745, 6; 351/6, 16, 39, 1; 356/340, 337, 338, 339

[56] References Cited

U.S. PATENT DOCUMENTS

| | | | |
|---|---|---|---|
| 3,589,800 | 6/1971 | Cardona | 351/1 X |
| 3,621,220 | 11/1971 | Ford | 356/340 X |
| 3,809,092 | 5/1974 | Abraham | 128/745 X |
| 3,944,341 | 3/1976 | Pomerantzeff | 351/6 X |
| 3,963,019 | 6/1976 | Quandt | 128/633 |
| 4,033,679 | 7/1977 | Sussman | 351/16 |
| 4,134,647 | 1/1979 | Ramos-Caldera | 351/6 |
| 4,259,948 | 4/1981 | Urban | 128/6 X |

FOREIGN PATENT DOCUMENTS

| | | | |
|---|---|---|---|
| 596821 | 9/1975 | Switzerland | 351/16 |
| 148200 | of 1962 | U.S.S.R. | 351/6 |
| 588972 | of 1978 | U.S.S.R. | 351/16 |

Primary Examiner—Robert W. Michell
Assistant Examiner—John C. Hanley
Attorney, Agent, or Firm—Chapin, Neal & Dempsey

[57] ABSTRACT

Method and apparatus are disclosed for measuring contaminants in aqueous humor without rupturing an examined eye. The apparatus includes a laser which projects a light beam through a gonioscopic lens into the aqueous humor of the examined eye. The light is scattered in the humor with a portion of the scattered light being reflected by the gonioscopic lens to an analyzing system. The system measures the diffusion constant of any contaminant in the aqueous humor and, by comparing the diffusion constant to a set of known diffusion constants, determines the composition of the macromolecules or the cells of the contaminant.

10 Claims, 2 Drawing Figures

METHOD AND APPARATUS FOR ANALYZING CONTAMINANTS IN AQUEOUS HUMOR

BACKGROUND

This invention relates to an apparatus which accurately identifies contaminants in the aqueous humor of a human eye.

Examination of the aqueous humor is a routine part of every eye examination. This reflects the realization by the clinician that alterations of the humor are a cardinal sign of disease, that the nature and magnitude of an observed change is a useful gauge of the type and severity of disease, and that the state of the aqueous is a useful monitor of the response to therapy. Alterations from normally clear aqueous humor occur in association with a variety of ocular diseases, e.g, infections, traumas and inflammations. Many of these diseases are major causes of visual loss. However, if detected early and properly diagnosed, such diseases can often be treated successfully to prevent further or permanent visual loss.

Accurate characterization of the composition of aqueous humor contaminants provides a basis for precise diagnosis of an ocular disease. Unfortunately, currently available techniques for analyzing aqueous contaminants often leave a lot to be desired.

For example, one known technique for accurately determining the composition of contaminants involves physical invasion of the examined eye with a syringe. This provides the much-needed information as to the types of aqueous contaminant, but involves a surgical procedure which carries some risk to the eye and which may itself alter the aqueous being studied. For this reason, such invasive samples are seldom taken without an urgent need for the results and are seldom repeated to follow the course of disease.

A need, therefore, exists for techniques which provide accurate identification and quantitation of aqueous humor contaminants by "non-invasive" examination of the human eye. As used herein, the term "non-invasive", in connection with the examination of a human eye, denotes examination of the eye which maintains the integrity of the cornea, i.e., where the tissue of the cornea is not ruptured.

Some non-invasive techniques have recently been invented for detecting changes in aqueous humor. One such technique, shown in U.S. Pat. No. 3,963,019 to Quandt, utilizes a beam of light projected through a patient's eye. An analyzer is positioned to detect the beam on its exit from the examined eye and compares the effect the aqueous humor had on the refraction of the beam against a norm. While the comparison roughly indicates a change in the glucose level in the aqueous humor, it does not characterize the macromolecules or cells of any aqueous contaminant.

Accordingly, it is the primary object of the present invention to provide a technique for analyzing the composition of contaminants in aqueous humor by non-invasive measurement of an examined eye.

It is a further object to provide a technique which accurately identifies and quantitates macromolecular or cellular contaminants in aqueous humor.

It is another object to provide a technique having the above-listed advantages, which can be used clinically with no greater risk or discomfort to the patient than routine slit-lamp gonioscopy.

It is yet another object to provide a technique for accurately identifying aqueous contaminants that is simple in design and easy to use.

These and other objects of the invention, as well as many of the attendant advantages thereof, will become more readily apparent when reference is made to the following description taken in conjunction with the accompanying drawings.

DETAILED DESCRIPTION OF THE PREFERRED EMBODIMENT

Figure 1:
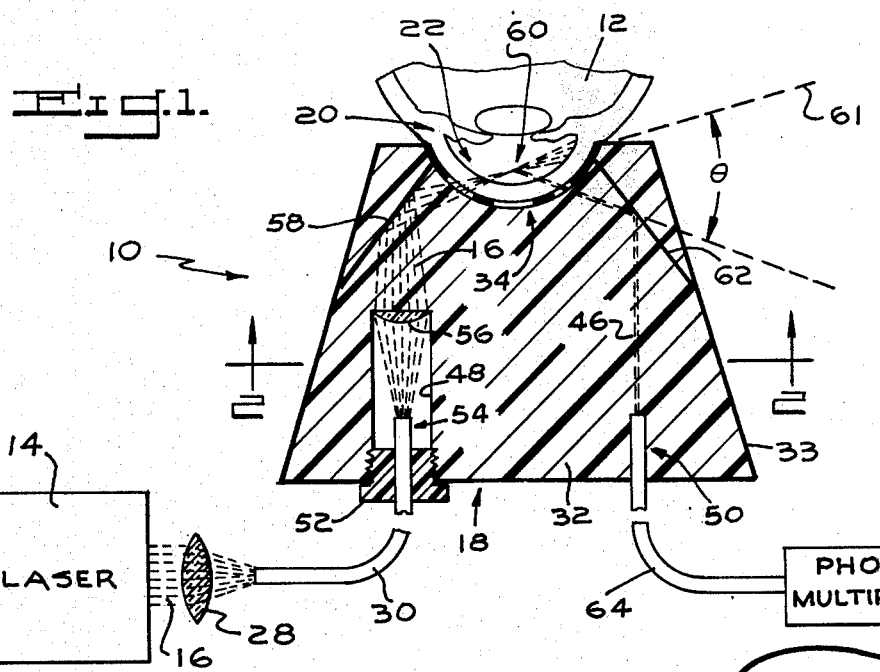
FIG. 1 is a schematic view of an optical examination system constructed in accordance with the present invention.
Figure 2:
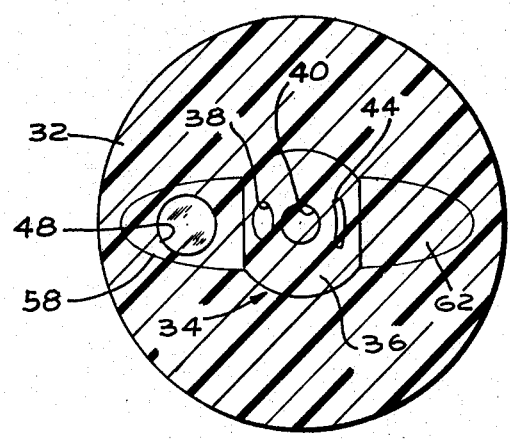
FIG. 2 is a fragmentary plan view of FIG. 1 taken along line 2—2.

Referring to the drawings, a system for measuring the composition of contaminants in aqueous humor is shown and generally designated by the reference numeral 10. The system is used for non-invasive examination of a human eye 12 and includes a laser 14 which projects a beam of light 16 through a modified Goldmann gonioscopic lens 18 into the anterior chamber 20 of the eye 12. The light 16 is scattered by any contaminants in the aqueous humor 22 in the chamber 20, with the scattered light being analyzed by a correlator 24 and computer 26 to determine the diffusion constant of each contaminant. The computer 26 is then used to compare the diffusion constant against a set of known diffusion constants to determine the composition of the contaminants in the aqueous humor 22.

Laser 14 is a continuous wave laser, such as Spectra Physics Model 145-01 which directs a beam 16 to a lens 28. From lens 28, the beam is focused upon an optical fiber 30 which carries the beam to the gonioscopic lens 18.

Gonioscopic lens 18 is a modified version of a standard Goldmann two-mirror gonioscopic lens (not shown) and includes a transparent plastic housing 32 with an opaque outer surface 33 and an integral concave recess (here, plastic contact lens 34). The modifications are of two types: first, the normally clear surface 36 in contact with the eye 12 is opaque except for a small entrance aperture 38 to admit the laser beam 16, a viewing port 40 to permit the clinician to see the scattering region, and an exit slit 44 to collect scattered light 46 from the region; and second, two bores 48, 50 are drilled into the housing 32. A cap 52 is threadedly attached to one end of bore 48 and slidably receives an end portion 54 of the fiber 30. A focusing lens 56 is attached to the other end of that bore.

As shown in FIG. 1, the laser beam 16 is projected through bore 48 onto the focusing lens 56. From the lens 56, the beam converges and is projected onto an input mirror 58. The mirror 58 reflects the beam 16 through the entrance aperture 38 to a focal point 60 near the center of the anterior chamber 20. The position of that point is adjusted by moving the fiber end portion 54 toward or away from the focusing lens 56. The position of the focal point is observed by using the viewing port 40 and is set at a position so that the scattered light 46 passing through the exit slit 44 originates from the adjustable focal point 60.

Viewing of the scattering region is accomplished by using a conventional slit-lamp biomicroscope (not shown) in connection with the viewing port 40 of surface 36. The biomicroscope also provides support for a patient's head and fixes the gaze of the patient's non-examined eye on a conventional built-in target lamp (not shown).

As shown in FIG. 1, the scattered light 46 passing through the exit slit 44 is light that has been scattered, by aqueous contaminants, from the focal point 60 at a scattering angle $\theta$ relative to a line of symmetry 61 for the beam 16. The light 46 is reflected by an output mirror 62 onto an output fiber 64 secured in the bore 50. The fiber 64 carries the light 46 to an assembly 66 of analyzing apparatus.

The analyzing apparatus 66 includes components that are structurally and functionally similar to the electrical analyzing apparatus of U.S. Pat. No. 3,621,220 to Norman C. Ford, Jr. That patent, however, does not deal with the examination of aqueous humor contaminants in a human eye. Further, the analyzing apparatus of that patent is insufficient to perform the analysis of aqueous contaminants performed by the present invention.

The present analyzer 66 includes a conventional sensor or photomultiplier 68, such as Hamamatsu Type R928, electrically connected to the commercially available signal correlator 24 (here, Model DC64 by Langley Ford Instruments) and a conventional oscilloscope 70.

Referring to FIG. 1, the scattered light 44 is carried by the optical fiber 64 to a light-receiving face (not shown) of the sensor 68, which transform the light into electrical pulses. The pulses are fed through a pulse amplifier discriminator 72 (here, commercially available Model PAD 1 by Langley Ford Instruments), which amplifies the pulses and selectively sends to the correlator 24 only those pulses above a certain amplitude.

Signal correlator 24 is more sophisticated than its counterpart of U.S. Pat. No. 3,621,220 in its capable output. Like its counterpart, the signal correlator 24 is constructed to have an output signal dependent upon the autocorrelation function of the pulses it receives from discriminator 72.

In the correlator 24, the number of pulses it receives is counted for each predetermined interval, e.g., one millisecond, the light 16 is scattered in the aqueous humor 22. The correlator utilizes these counts to solve the following autocorrelation function $G(K\Delta t)$:

$$G(K\Delta t) = \sum_{i=1}^{i=x} n_i n_{i+k} \quad \text{(Equation 1)}$$

where:
$\Delta t$: the predetermined time interval;
n = the number of pulses during a particular time interval;
i = an indexing number going from 1 to the total number of intervals;
x = total number of intervals; and
K = an integer going from 1 to 64, such that the function is solved 64 times; e.g., the first solution is:

$$G(\Delta t) = \sum_{i=1}^{i=x} n_i n_{i+1}$$

and the last of the sixty-four solutions is $$G(64\Delta t) = \sum_{i=1}^{i=x} n_i n_{i+64}.$$

Thus, in the preferred embodiment, correlator 24 solves equation 1 sixty-four times. The correlator plots the solutions into a curve, which is shown on oscilloscope 70, and describes the curve to the computer 26, which is a conventional digital computer such as Commodore Model PET 2001-32N. This is always the procedure irrespective of whether there is a single contaminant or a plurality of contaminants in an examined eye 12.

Before the present invention can be used to analyze the macromolecules, i.e., molecules having a molecular weight of at least 500) or cells of aqueous contaminant in a patient's eye 12, certain information must be stored in the computer 26 for comparison purposes. This is done by taking each of the commonly known contaminants that occur in ocular diseases and determining the diffusion constants D of those contaminants by using the following autocorrelation function $G(K\Delta t)$ for the variation in intensity of the light scattered by a single type of macromolecular or cellular contaminant in an aqueous humor 22:

$$G(K\Delta t) = A + Be^{-2DC^2(k\Delta t)} \quad \text{(Equation 2)}$$

where:
A and B are constants that depend upon the duration of the measurement and details of the system 10 such as the size of the beam 16 at focal point 60, the size of exit slit 44, the diameter of the output fiber 64, and the distance from the focal point 60 to the output fiber;
e = the base of natural logarithms;
c = $(4\pi/\lambda)$ sin $\theta/2$, where $\lambda$ is the wavelength of the light 16 in the aqueous humor 22 and $\theta$ is the scattering angle;
$\Delta t$ = predetermined time interval; and
K = integers from 1→64, such that Equation 2 is solved sixty-four times.

The diffusion constant D and the constant B are determined by standard curve fitting routines where the function of $G(K\Delta t)$ is plotted in a curve having the natural log of the function (minus the constant A) as its ordinate and the time interval $(K\Delta t)$ as its abscissa. The known diffusion constants are then stored in the computer 26.

The present invention is then ready for analysis of the aqueous contaminants of any subsequently examined eye by using the following technique:

The patient's eye 12 is examined by the present system 10, with the information obtained by correlator 24, i.e., the 64 values of Equation 1, being sent to the computer 26 in the form of electrical signals.

Since there may be more than one type of contaminant in the eye 12, the computer is programmed with the following equation for the autocorrelation function $G(K\Delta t)$:

$$G(K\Delta t) = A' + \left[ B_1 e^{-D_1 C^2(K\Delta t)} + B_2 e^{-D_2 C^2(K\Delta t)} + \ldots B_n e^{-D_n C^2(K\Delta t)} \right]^2 \quad \text{(Equation 3)}$$

where:
$A'$ = a constant;
$B_1, B_2 \ldots B_n$ = constants each dependent upon the concentration of a particular macromolecular of cellular contaminant in the aqueous humor 22; e.g., if there are only two types of contaminants, only two terms of the B coefficients will have values >0; $D_1$, $D_2$, $D_n$=diffusion constants for each potential contaminant; K=the 64 integers used by correlator 24 in solving Equation 2.

By using a standard curve fitting program, the computer 26 plugs in the previously stored diffusion constants for known contaminants and solves for A', $B_1$ ... $B_n$ by trying different values for A', $B_1$ ... $B_n$ until a particular combination of values for A', $B_1$ ... $B_n$ best approximates the data for the 64 intervals. From the relative values of $B_1$ ... $B_n$ the concentrations of the contaminants are calculated by the computer 26.

It should be understood by those skilled in the art that the system 10 can be used to analyze contaminants in vitreous humor of an eye 12 by focusing the focal point 60 in the vitreous humor.

It should also be understood that obvious structural modification of the disclosed embodiment can be made without departing from the spirit of the invention. For example, a single unit for performing the functions of computer 26 and correlator 24 can be utilized rather than the present two units 24, 26. Accordingly, reference should be made primarily to the accompanying claims rather than to the specification to determine the scope of the invention.

Having thus described the invention, what is claimed is:

1. An apparatus for measuring contaminants in humor of an eye by non-invasive measurement of the eye, the apparatus comprising:
   (a) a continuous wave laser for producing light beams of known wave length;
   (b) projection means for directing and converging a light beam from the laser to a focal point in the humor, said projection means including a gonioscopic lens having a transparent housing with an opaque outer surface and an attached concave recess adapted to fit over the cornea of the examined eye, wherein the concave recess is substantially opaque except for a transparent entrance port to admit the laser beam into the humor, a transparent viewing port to permit a clinician to view scattering of the beam in the humor, and a transparent exit port to collect scattered light from the humor; and
   (c) means for analyzing the composition of macromolecular contaminants in the humor by analyzing the diffusion constant of each contaminant by using the light scattered from the focal point at a particular scattering angle $\theta$ relative to a line of symmetry for the beam in the humor.

2. The apparatus of claim 1 wherein:
   (a) the gonioscopic lens further includes an input mirror for directing the beam into the humor and an output mirror for directing the scattered light to the analyzing means; and
   (b) the projection means includes a first optical fiber for directing the beam onto the input mirror and through the entrance port into the humor and a second optical fiber for directing the scattered light from the output mirror to the analyzing means, said fibers having end portions that are respectively received in separate bores of the housing of the gonioscopic lens.

3. The apparatus of claim 2 wherein the projection means further includes adjustment means for selectively adjusting the position of the focal point in the humor.

4. The apparatus of claim 2 wherein said end portion of the first optical fiber is movable within its associated bore of the gonioscopic lens to adjust the position of the focal point in the humor.

5. An apparatus for measuring contaminants in humor of an eye by non-invasive measurement of the eye, the apparatus comprising:
   (a) a continuous wave laser for producing light beams of known wave length;
   (b) projection means for directing and converging a light beam from the laser to a focal point in the humor;
   (c) means for analyzing the composition of macromolecular contaminants in the humor by measuring the diffusion constant of each macromolecular contaminant by using the light scattered from the focal point at a particular scattering angle $\theta$ relative to a line of symmetry for the beam in the aqueous humor;
   (d) wherein the projection means comprises a gonioscopic device having:
      (i) a housing having an input mirror for directing the beam into the humor;
      (ii) said housing having an attached concave recess adapted to fit over the cornea of the examined eye, wherein the recess is substantially opaque except for a plurality of transparent ports, one of said ports being an entrance port to admit the beam relected from the input mirror into the humor, and another of said ports being an exit port to collect scattered light from the humor; and
      (iii) said housing having an output mirror for directing the scattered light to the analyzing means.

6. The apparatus of claim 5 wherein the projection means further includes a first optical fiber for directing the beam from said laser onto the input mirror, said fibre having an end portion that is slidably received within said housing for said gonioscopic device and movable therein to adjust the position of the focal point in the humor.

7. The apparatus of claim 6 wherein the projection means further includes a focusing lens between said end portion of said first fiber and said input mirror for focusing the beam to the focal point in the humor, said focusing lens being attached to said housing for said gonioscopic device.

8. A method for analyzing the composition of contaminants in aqueous humor by non-invasive measurement of an examined eye, the method comprising:
   (a) directing and focusing a laser beam of known wavelength through a gonioscopic lens to a focal point in the aqueous humor;
   (b) collecting light scattered from the focal point at a scattering angle $\theta$ relative to a line of symmetry for the beam in the aqueous humor;
   (c) transforming the collected light into electrical pulses;
   (d) producing electrical signals representative of the following autocorrelation function $G(k\Delta t)$ for only those pulses above a predetermined amplitude:

$$G(k\Delta t) = \sum_{i=1}^{i=x} n_i n_{i+k}$$

where:

$\Delta t$ = a predetermined time interval;

n = the number of pulses during a particular time interval;

i = an indexing number going from 1 to the total number of intervals X the scattered light is collected; and K = a plurality of successive integers starting with the integer 1;

(e) computing the composition of contaminants in the aqueous humor by using standard curve fitting routines for the following alternative equation for the autocorrelation function $G(K\Delta t)$ to solve for $B_1, B_2 \ldots B_n$ and $D_1, D_2 \ldots D_n$:

$$G(K\Delta t) = A' + [B_1 e^{-D_1 C^2(K\Delta t)} + B_2 e^{-D_2 C^2(K\Delta t)} + \ldots B_n e^{-D_n C^2(K\Delta t)}]^2$$

where:

$A'$ = a constant;

$B_1, B_2 \ldots B_n$ = constants each dependent upon the concentration of a particular type of contaminant in the aqueous humor;

$D_1, D_2, D_n$ = diffusion constants for each potential contaminant; and e = the base of natural logarithms;

wherein known diffusion constants for contaminants are substituted for $D_1, D_2 \ldots D_n$ and $B_1, B_2 \ldots B_n$ are assigned different values until the values of the alternative equation best approximate the measured electrical signals.

9. The method of claim 8 wherein the contaminants analyzed are macromolecular.

10. The method of claim 8 wherein the contaminants analyzed are cellular.

* * * * *